United States Patent [19]

Semonský et al.

[11] 4,237,270
[45] Dec. 2, 1980

[54] DERIVATIVES OF CARBOXYALKYL IMINO- AND THIOXO-BARBITURIC ACIDS

[75] Inventors: Miroslav Semonský; Rudolf Kotva; Antonin Černy; Jiří Krepelka; Vojtech Pujman; Oskar Andrysek, all of Prague, Czechoslovakia; Hana Veselá, deceased, late of Prague, Czechoslovakia, by Jiri Vesely, heir

[73] Assignee: SPOFA, United Pharmaceutical Works, Prague, Czechoslovakia

[21] Appl. No.: 898,220

[22] Filed: Apr. 20, 1978

Related U.S. Application Data

[63] Continuation-in-part of Ser. No. 658,080, Feb. 13, 1976, abandoned.

[30] Foreign Application Priority Data

Feb. 17, 1975 [CS] Czechoslovakia ............... 101675-75

[51] Int. Cl.³ .......................................... C07D 239/54
[52] U.S. Cl. ..................................... 536/18; 544/302; 544/320; 544/321
[58] Field of Search ...................... 544/302, 320, 321; 536/18

[56] References Cited

U.S. PATENT DOCUMENTS 2,153,729  4/1939  Volwiler et al. ..................... 544/306
2,899,435  8/1959  Brandstrom ......................... 544/306

OTHER PUBLICATIONS

Johnson et al., Chem. Abstracts, vol. 7 (1913) p. 1701.
Rericha et al., Chem. Abstracts, vol. 45 (1951) col. 8017.

Primary Examiner—Paul M. Coughlan, Jr.

[57] ABSTRACT

5-Carboxyalkyl-2-iminobarbituric and 5-carboxyalkyl-2-thioxobarbituric acids and derivatives thereof are prepared either by condensation of a triester of a tricarboxylic acid with a thio or imino diamide to yield an ester which is saponified, the desired compound being obtained by liberation with a mineral acid from an ammoniacal medium containing the saponified ester. Alternatively, free tricarboxylic acids may be substituted for the triesters. The compounds described herein have evidenced a therapeutic effect in animals having transplanted tumors, and have inhibited tumor growth and lengthened the life of animals and humans.

6 Claims, No Drawings

DERIVATIVES OF CARBOXYALKYL IMINO- AND THIOXO-BARBITURIC ACIDS

This application is a continuation-in-part of our co-pending application Ser. No. 658,080, filed Feb. 13, 1976, now abandoned.

This invention relates to barbituric acids and derivatives thereof. More particularly, the present invention relates to 5-carboxyalkyl-2-iminobarbituric and 5-carboxyalkyl-2-thioxobarbituric acids and derivatives thereof.

During the past two decades, medical researchers have made significant advances in arresting tumorous growths in animals and humans. Nonetheless, much remains to be done and workers in the art have continued to focus their interest upon the development of novel compositions evidencing characteristics suitable for that purpose.

In accordance with the present invention, novel barbituric acids of the general formula

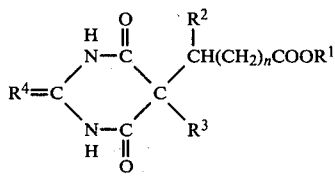

are described wherein $R^1$ is selected from the group consisting of hydrogen, a straight or branched chain alkyl group having from 1-7 carbon atoms, $R^2$ is selected from the group consisting of hydrogen and a straight or branched chain alkyl group having from 1-5 carbon atoms, $R^3$ is selected from the group consisting of hydrogen, a phenyl group, and a straight or branched chain alkyl group having from 1-5 carbon atoms, and $R^4$ is selected from the group consisting of sulfur and an imino group, n being an integer from 0-6.

Studies have revealed that the foregoing compounds and salts thereof, when administered perorally or parenterally in the form of a microsuspension or salt solution, manifest significant biological characteristics and evidence limited toxicity. More specifically, the described compounds have evidenced a therapeutic effect in animals having transplanted tumors and have inhibited tumor growth and lengthened the life of animals and humans. Additionally, it has been found that the use of the novel compositions in combination with clinically used cytostatics, such as 5-fluorouracil, cyclophosphamide, vincristine, actinomycin D, methotrexate and the like, exhibit therapeutic effects in animals and humans having tumors beyond the levels anticipated, that is, beyond additive levels, thereby permitting the attainment of novel therapeutic levels without increasing toxicity.

The compounds described herein may be prepared by condensation of a triester of a tricarboxylic acid having the general formula

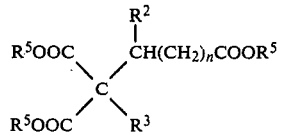

wherein $R^5$ is selected from the group consisting of methyl and ethyl groups and $R^2$, $R^3$, and n are as indicated in formula (1) above with a compound of the general formula

wherein $R^4$ is as indicated above in formula (1). More specifically, in those cases wherein $R^4$ is an imino group, guanidine hydrochloride may conveniently be employed as the condensation agent and when $R^4$ is sulfur, thiourea is employed as the condensation agent. The condensation reaction is effected in the presence of a sodium alkoxide, typically sodium ethoxide. The crude condensation product is initially isolated by conventional techniques and, subsequently, reacted with sodium hydroxide to saponify the ester. The desired compound having the general formula (1) in which $R^1$ represents a hydrogen atom is liberated from the resultant solution by means of a mineral acid, purified by dissolution in aqueous ammonia and again liberated by a mineral acid. The action of the resultant acid with a compound such as a thionyl chloride in an alcoholic medium yields an ester.

The acids of formula (1) wherein $R^1$ is a hydrogen atom may readily be converted to salts of the corresponding carboxylic acid or into an addition product of the acid with organic bases by reaction with one molecular equivalent of alkali metal hydroxide, bicarbonate or carbonate, or with N-methylglucosamine or diethanolamine, respectively. The use of the molecular equivalents of an alkali metal hydroxide yields a salt containing two atoms of the alkali metal, such as a disodium salt.

An alternative procedure for preparing compounds of formula (1) involves the use of free tricarboxylic acids corresponding to compounds of formula (2), above, such end being attained by reaction with N,N$^1$-dicyclohexylcarbodiimide as a condensation agent. This procedure is more time-consuming than the foregoing procedure and results in lower yields. Esterification may again be effected by the addition of thionyl chloride with an excess of the corresponding alcohol, the mixture being cooled to a temperature ranging from $-5°$ C. to $-40°$ C.; the resultant reactive derivative reacting with the alcohol.

The compounds designated (2) above may conveniently be prepared by reaction of sodiomalonate or its alkyl or aryl substituted derivatives with the corresponding methyl or ethyl haloalkanecarboxylates, typically bromoalkanecarboxylates. A particularly useful compound suitable for use in the practice of the present invention, the triethyl ester of α-carboxypimelic acid, is prepared by the condensation of ethyl δ-bromovalerate with dialkyl sodiomalonate as described by Karrer et al, Helv. Chim. Acta 27, 1944, p. 237.

The acids and salts thereof prepared in accordance with the present invention are crystalline in nature and essentially stable in solid state. In aqueous solution, it has been found that these compounds, upon exposure to atmospheric oxygen, particularly those compounds wherein $R^4$ is an imino or amino group, are unstable. However, in the absence of atmospheric oxygen, as for example in the presence of nitrogen, the aqueous solutions are stable.

The compounds obtained herein may be therapeutically applied in the form of tablets, which may be coated, for oral administration, or in the form of a microsuspension in a pharmaceutically non-toxic vehicle, such as an aqueous methyl cellulose solution. The described compounds may also be administered parenterally in the form of aqueous solutions of their salts, such as the disodium salts, or of their adducts with organic bases such as diethanolamine. These solutions may conveniently be prepared immediately prior to application in the form of dry ampoules or in the case of the prepared solutions for injection by storage in injection ampoules which exclude atmospheric oxygen.

Based upon experimental studies, it has been determined that the compositions described herein may be employed as a cytostatic in varying dosages dependent upon the specific composition employed. Thus, for example, the composition described in example (1) may be employed in daily dosages ranging from 200–5000 mg orally or in doses ranging from 100–1000 mg intramuscularly, in adults, for the treatment of malignant tumorous diseases.

Examples of the practice of the present invention are set forth below. It will be appreciated by those skilled in the art that the exemplary embodiments are for purposes of exposition only and are not to be construed as limiting.

EXAMPLE 1

2-Imino-5-(4-carboxybutyl)barbituric acid
(2-amino-6-hydroxy-5-(4-carboxybutyl)-3,4-dihydro-4-oxopyrimidine)

239 grams (2.50 mol) of guanidine hydrochloride and 362 grams (1.25 mol) of the triethyl ester of α-carboxypimelic acid were added at 40°–45° C. in a nitrogen ambient to a stirred solution of sodium ethoxide, the latter being prepared by adding 86.5 grams (3.75 mol) of sodium to 2500 ml of absolute ethanol. The reaction mixture was stirred for 4 hours at room temperature and set aside overnight. Next, the ethanol was distilled off under reduced pressure and the resultant ester saponified overnight with 2500 ml (1.25 mol) of 0.5 N sodium hydroxide at 20° C. The, the resultant solution was boiled, filtered with charcoal, and the hot filtrate acidified with a dilute (1:1) hydrochloric acid solution to a pH of 3. After cooling, the resultant compound was filtered, washed with water, and dried at room temperature, so yielding 270 grams (82.3%) of 2-imino-5-(4-carboxybutyl)barbituric acid containing 13% crystallized water which corresponds with the dihydrate of the acid. The product was next dissolved in a 50-fold excess of dilute ammonia (about 1:100), decolorized with activated carbon and acidified to a pH of 3 with dilute hydrochloric acid, so yielding the product in the form of colorless needles, m.p. 318°–320° C. (decomposition).

The monosodium salt of the above-prepared barbituric acid was next prepared by dissolution of 5.68 grams (25 mmol) of the acid in 250 ml (25 mmol) of boiling of 0.1 N sodium hydroxide in a nitrogen ambient. The solution was concentrated under reduced pressure to about 30 ml, the salt crystallizing in the form of colorless crystals containing about 5% solvent, m.p., 200°–205° C. (decomposition).

The disodium salt of the above-prepared barbituric acid was prepared by dissolving 5.68 grams (25 mmol) of the acid in 50 ml (50 mmol) of 1 N sodium hydroxide at room temperature in a nitrogen ambient. Evaporation of the solvent at reduced pressure yielded the disodium salt as a colorless microcrystalline compound, m.p. 260°–265° C. (decomposition). The compound is soluble in water, the 1% solution evidencing a pH of 11.5.

The addition salt of the described barbituric acid with diethanolamine was prepared by dissolving 2.27 grams (10 mmol) of the acid in a solution of 1.58 grams (15 mmol) of diethanol-amine in 100 ml of boiling water in a nitrogen ambient. The solution was subjected to reduced pressure and concentrated to 20 ml. Next, it was diluted with 200 ml of hot ethanol and permitted to cool. The diethanol ammonium salt was obtained in the form of colorless needles melting at 167°–169° C. (decomposition).

Utilizing the corresponding malonic acid derivatives of the general formula (2), above, the following compounds of the general formula (1) were prepared in accordance with the procedure of Example 1:

2-imino-5-(carboxymethyl)barbituric acid, m.p. 290°–292° C. (decomposition)-(water);
2-imino-5-(2-carboxyethyl)barbituric acid, m.p. 320°–325° C. (decomposition)-(water);
2-imino-5-(3-carboxypropyl)barbituric acid, m.p. 311°–312° C. (decomposition)-(water);
2-imino-5-(1-carboxybutyl)barbituric acid, m.p. 241°–242° C. (decomposition)-(water);
2-imino-5-(5-carboxypentyl)barbituric acid, m.p. 291°–293° C. (decomposition)-(water);
2-imino-5-(6-carboxyhexyl)barbituric acid, m.p. 296°–298° C. (decomposition)-(water);
2-imino-5-methyl-5-(4-carboxybutyl)barbituric acid, m.p. 299°–301° C. (decomposition)-(water);
2-imino-5-ethyl-5-(4-carboxybutyl)barbituric acid, m.p. 278°–280° C. (decomposition)-(water);
2-imino-5-n-propyl-5-(4-carboxybutyl)barbituric acid, m.p. 295°–297° C. (decomposition)-(water);
2-imino-5-n-butyl-5-(4-carboxybutyl)barbituric acid, m.p. 306°–307° C. (decomposition)-(water); and
2-imino-5-phenyl-5-(4-carboxybutyl)barbituric acid, m.p. 304°–307° C. (decomposition)-(water).

EXAMPLE 2

2-imino-5-(4-ethoxycarbonylbutyl)barbituric acid, and
(2-amino-6-hydroxy-5-(4-ethoxycarbonylbutyl)-3,4-dihydro-4-oxopyrimidine)

12.1 grams (0.11 mol) of thionyl chloride was added dropwise to 130 ml of ethanol while stirring and cooling to a temperature ranging from −5° to −40° C. Then, 22.72 grams (0.1 mol) of 2-imino-5-(4-carboxybutyl)barbituric acid was added portionwise and the resultant suspension stirred for 2 hours at 40° C. and then for 2 hours while refluxing, the starting compound being dissolved. Next, the solvent was distilled off under reduced pressure and the residue mixed with 230 ml of water, the resultant suspension being neutralized with sodium hydrogen carbonate. The separated product was then filtered, yielding 23.8 grams (93%) of 2-imino-5-(4-ethoxycarbonylbutyl)barbituric acid. Crystallization from 50% aqueous ethanol yields colorless crystals having a m.p. within the range of 277°–279° C. (decomposition).

Utilizing the corresponding alcohols in the esterification process, the following esters of formula (1) were prepared in accordance with the procedure of Example 2:

2-imino-5-(4-methoxycarbonylbutyl)barbituric acid, m.p. 267°–270° C. (dimethylformamide-methanol);
2-imino-5-(4-n-butoxycarbonylbutyl)barbituric acid, m.p. 274°–276° C. (chloroform-methanol);
2-imino-5-(4-n-heptyloxycarbonylbutyl)barbituric acid, m.p. 269°–272° C. (ethanol).

EXAMPLE 3

2thioxo-5-n-butyl-5-(4-carboxybutyl)barbituric acid

A solution comprising 6.89 grams (0.02 mol) of the triethylester of α-butyl-α-carboxypimelic acid in 60 ml of ethanol was added with 4.57 grams (0.06 mol) of thiourea to a sodium ethoxide solution prepared by reacting 1.38 grams (0.06 mol) of sodium with 60 ml of ethanol. The mixture was refluxed for 3 hours while stirring. Then, the solvent was distilled off under reduced pressure, the residue dissolved in 25 ml of water and the solution permitted to stand overnight at room temperature. Acidification of the solution with dilute hydrochloric acid to a pH of 2 yields an oily product which crystallizes from 50% aqueous ethanol, so yielding the hemihydrate of 2-thioxo-5-n-butyl-5-(4-carboxybutyl)barbituric acid, m.p. 53°–55° C. Using corresponding malonic acid derivatives of formula (2) above, the following derivatives of 2-thioxobarbituric acid of formula (1) were obtained by the procedure of Example 3:

2-thioxo-5-(4-carboxybutyl)barbituric acid, m.p. 206°–208° C. (ethanol-hexane);
2-thioxo-5-ethyl-5-(4-carboxybutyl)barbituric acid, m.p. 166°–167° C. (water); and
2-thioxo-5-phenyl-5-(4-carboxybutyl)barbituric acid, m.p. 125°–127° C. (aqueous ethanol).

EXAMPLE 4

2-amino-6-hydroxy-5-(4-carboxybutyl)-3-4-dihydro-4-oxopyrimidine

The above solution was prepared as described herein and was chosen for study. In a human tumor cell suspension (in vitro) in concentrations ranging from 0.01–10 µg/ml two peak effects were observed, one at 0.01 µg/ml and the other at 1 µg/ml.

In cells of human ovarian ascitic carcinomas, the oxopyrimidine produced moderate antineoplastic effects. When added to a cell suspension together with a known cytostatic agent, a marked potentiating effect was observed as compared with the other cytostatic alone or the noted oxopyrimidine alone. This potentiation of the antineoplastic efficiency was proved in a series of 46 ovarian ascitic carcinomas for the following compositions: cyclophosphamide, butocine, methotrexate, 5-fluorouracil, actinomycin D, and L-phenyl-alanine mustard.

In 11 women, clinically and by laboratory testing with $^{125}$I-5-iodo-$2^1$-deoxyaridine, resistance to methotrexate dosed up to 30 ml/m$^2$ was proven. Autoradiograms of ascitic cells with $^3$H-methotrexate (in vitro incubation) showed quantitatively 10%, at most, of the number of grains per cell in comparison with a sensitive group. Addition of the above-identified oxopyrimidine during incubation raised the average number of grains per cell to values exceeding those found in a sensitive group.

EXAMPLE 5

Quantitative autoradiography of tumors with known cytostatics and the oxopyrimidine of Example 4 were studied. The experimentation was performed in vitro with Yoshida's ascitic sarcoma in rats and with Lewis' lung carcinoma in mice. The cytostatics 5-fluorouracil-$^3$H and actinomycin D-$^3$H were used. The cells were incubated for 1 hour at 37° C. either with one or the other cytostatic alone or in combination with 1 µg/ml of the oxopyrimidine of Example 4. The number of labeled cells per 600–1000 cells in a smear were counted. The results are set forth in Table I, below.

TABLE I

| Tumor | Cytostatic | Percent increase in number of labeled cells | Significance (p) |
| --- | --- | --- | --- |
| Yoshida's ascitic sarcoma | Actinomycin D | 217 | 0.005 |
|  | 5-Flourouracil |  |  |
|  | Series #1 | 118 | 0.05 |
|  | Series #2 | 129 | 0.005 |
| Lewis' lung carcinoma (suspension) | Actinomycin D | 231 | 0.005 |
|  | 5-Fluorouracil | 98.6 | not significant |

A further series of quantitative autoradiography with $^3$H-methotrexate showed an increase by 36% in the number of labeled cells of Crocker's ascitic sarcoma 180 after addition of the oxopyrimidine of Example 4 in the above-noted concentration at the significance level p.=0.05.

EXAMPLE 6

This example describes the effect of 2-amino-6-hydroxy-5-(4-carboxybutyl)3-4-dihydro-4-oxopryimidine on the elevation of radioactivity in tumors in experimental animals after administration of labeled cytostatics. The testing objects included the solid tumor (Crocker's ascitic sarcoma 180), Lewis' solid lung tumor and Gardner's lymphosarcoma. Labeled cytostatics included $^3$H-methotrexate and $^3$H-fluorouracil. The oxopyrimidine dosed to levels of 100 mg/kg and 200 mg/kg was injected subcutaneously at intervals ranging from 96 to 1.5 hours before intraperitoneal injection of a labeled cytostatic filled with a carrier to therapeutic doses. After 2 hours, the tumor was extirpated and the radioactivity was measured with the aid of liquid scintillatoes. The results were expressed in percent compared with animals that had received the same labeled cytostatic alone without the addition of the oxopyrimidine. In each case groups of 6 animals were used.

It was determined that the oxopyrimidine, when administered in advance at an interval greater than 24 hours did not affect the radioactivity level in the tumor. However, in those cases where the oxopyrimidine was injected at intervals of 24 hours, 2 hours and 90 minutes prior to the injection of labeled cytostatic, the radioactivity levels in tumors in the experimental animals was elevated significantly. The results are set forth in Table II below.

TABLE II

| Tumor | Oxopyrimidine mg/kg s.c. | Interval between injection of other cytostatic | Other cytostatic | % elevation radioactivity | Significance (p) |
| --- | --- | --- | --- | --- | --- |
| Crocker's |  |  |  |  |  |

TABLE II-continued

| Tumor | Oxopyrimidine mg/kg s.c. | Interval between injection of other cytostatic | Other cytostatic | % elevation radioactivity | Significance (p) |
|---|---|---|---|---|---|
| ascitic sarcoma 180 | 100 | 24 hours | $^3$H-methotrexate | 32 | 0.05 |
| Gardner's lymphosarcoma | 150 | 2 hours | $^3$H-methotrexate | 31 | 0.05 |
| Lewis'lung carcinoma | 200 | 90 minutes | $^3$H-5-fluouracil | 42 | 0.05 |

In light of the data presented herein, it is apparent that the use of the oxopyrimidine may be employed in human therapeutic applications as a cytostatic in daily doses ranging from 200–500 mg orally, or from 100–1000 mg intramuscularly, in adults, for the treatment of malignant tumorous diseases. This same range of dosages obtains when used in combination with conventional cytostatics such as 5-fluorouracil, actinomycin D, methotrexate and the like.

Further studies revealed that delta-(2-amino-6-hydroxy-3,4-dihydro-4-oxo-5-pyrimidinyl) valeric acid (DMV) and the monosodium and disodium salts thereof inhibited the growth of transplanted tumors in laboratory animals, enhanced the antitumorous effect of conventional cytostatic drugs such as cyclophosphamide, vincristine, adriaomycin and the like, and influenced the pharmacokinetics of cytostatic drugs so that the cytostatic drug penetrates tumorous cells more readily.

EXAMPLE 7

The efficacy of the valeric acid derivative on the tumor weight and life span of animals was demonstrated in mice bearing transplantable tumors, namely, Krebs-2-ascitic tumor or an ascitic tumor herein identified as "S-37 ascitic tumor." The results are set forth in Table III below and a review thereof reveals that the valeric acid derivative decreased the tumor weight and prolonged the survival time.

TABLE III

| Dosage and tumor | Tumor weight on Day 10 after transplantation (Mean ± S.E.M.) | | Life span after transplantation (geometric mean and fiducial limits at P = 0.95) | |
|---|---|---|---|---|
| | Controls | Treated | Controls | Treated |
| Krebs asc.tu. 100 mg/kg s.c. x8 (Days 1–5; 7–9 after transplant.) S-37 asc.tu. | 5.7g ± 0.6 100% | 4.4g ± 0.2 77% | 24 days (22–26) 100% | 32 days (28–35) 133% |

TABLE III-continued

| Dosage and tumor | Tumor weight on Day 10 after transplantation (Mean ± S.E.M.) | | Life span after transplantation (geometric mean and fiducial limits at P = 0.95) | |
|---|---|---|---|---|
| | Controls | Treated | Controls | Treated |
| 100 mg/kg s.c. x2 (Day 1 and 4 after transplant) (10 animals per group) | 5.1g ± 0.4 100% | 3.1g ± 0.3 61% | 20 days (18–22) 100% | 22 days (18–26) 110% |

A similar effect was observed when the monosodium and disodium salts of DMV were injected in mice bearing S-37 ascitic tumor, as Table IV shows.

TABLE IV

| Treatment (on Days 1–5 and 7–9 after transpl.) | Tumor weight (Mean ± S.E.M.) | % of Control | Number animals |
|---|---|---|---|
| Control | 6.2g ± 0.3 | 100% | (10) |
| DMV acid 100 mg/kg s.c. × 8 | 3.8g ± 0.4 | 61% | (8) |
| DMV monosodium salt 112 mg/kg s.c. × 8 | 3.4g ± 0.5 | 55% | (7) |
| DMV disodium salt 120 mg/kg s.c. × 8 | 4.1g ± 0.9 | 66% | (7) |

The effect of DMV on the antitumorous action of cytostatic drugs was demonstrated with the experiments in which the weights of Krebs and S-37 ascitic tumors were compared on the 10th day after transplantation in groups of mice (10 animals per group) treated either with physiological saline, or the cytostatic alone, or DMV alone, or both the cytostatic and DMV. The results of these experiments are presented in Table V. It can be recognized therefore that the used dosage of cyclophosphamide, vincristine, or adriamycin produced no, or an insignificant, tumor-growth inhibiting effect when administered alone, but a significant tumor-growth inhibiting effect when administered conjointly with DMV.

TABLE V

| Tumor | Treatment | Tumor weight (Mean ± S.E.M.; percentage related to the Control group) | | | |
|---|---|---|---|---|---|
| | | Control | Cytostatic alone | DMV alone | Cytostatic + DMV |
| Krebs-2 | Cyclophosphamide 35 mg/kg s.c. x2 (Days 1 and 4) DMV 100 mg/kg s.c. x2 (Days 1 and 4) | 5.6g ± 0.4 100% | 5.7g ± 0.4 102% | 5.2g ± 0.6 93% | 3.9g ± 0.2 70% |
| Krebs-2 | Cyclophosphamide 35 mg/kg s.c. x2 (Days 1 and 4) DMV 50 mg/kg s.c. x8 (Days 1–5; 7–9) | 6.1g ± 0.7 100% | 6.2g ± 0.4 101% | 5.5g ± 0.6 90% | 4.3g ± 0.4 70% |
| Krebs-2 | Vincristine | | | | |

TABLE V-continued

| Tumor | Treatment | Control | Cytostatic alone | DMV alone | Cytostatic + DMV |
|---|---|---|---|---|---|
| | | Tumor weight (Mean ± S.E.M.; percentage related to the Control group) | | | |
| Krebs-2 | 0.25 mg/kg s.c. x2 (Days 1 and 4) DMV 160 mg/kg s.c. x2 (Days 1 and 4) Adriamycin 1.25 mg/kg s.c. x2 (Days 1 and 4) DMV | 6.3g ± 0.5 100% | 6.2g ± 0.8 98% | 5.7g ± 0.7 90% | 4.1g ± 0.6 65% |
| S-37 | 100 mg/kg s.c. x2 (Days 1-5; 7-9) The same | 6.4g ± 0.3 100% 7.2g ± 0.4 100% | 5.6g ± 0.2 88% 7.0g ± 0.3 97% | 3.3g ± 0.3 52% 4.9g ± 0.7 68% | 2.0g ± 0.3 31% 2.9g ± 0.3 40% |

The action of DMV accelerating the penetration of cytostatics into tumorous cells was demonstrated with two experiments performed in mice with Krebs ascitic tumor ten days after its inoculation.

In one experiment, ninety minutes after the subcutaneous injection of 200 mg/kg Damvar (labeled Fluorouracil 5-Fluorouracil-6-$^3$H) was injected s.c. in the amount of 30 $\mu$Ci per animal. Two hours later the mice were killed, and the radioactivity present in the cells of their ascites was measured. The control animals were treated in the same way, but instead of DMV they were given a subcutaneous injection of saline. Table VI presents the results showing that the radioactivity from labeled Fluorouracil was incorporated into the tumorous ascitic cells in the DMV-treated animals in a higher degree than in the control animals.

TABLE VI

| | Controls | DMV-treated |
|---|---|---|
| Counts 10$^{-5}$ per cell per minute | 126 ± 16 (7 animals) | 203 ± 28 (6 animals) |

In the other experiment, the mice were injected either with DMV 200 mg/kg or saline s.c., and 90 minutes later were killed. Their ascites were taken, added 5 $\mu$Ci 5-Fluorouracil-6-$^3$H per 1 ml and incubated at 37° C. during 30 or 60 minutes. Thereafter the cells were isolated from the ascitic fluid, washed, and the radioactivity present in the cells was measured. The mean radioactivities present in the tumorous cells of each group are given in Table VII. These values show that the tumorous cells from the DMV-treated animals incorporated the Fluorouracil radioactivity more rapidly than the cells from the control animals.

TABLE VII

| Duration of the incubation | Counts · 10$^{-5}$ per cell per minute (Mean ± S.E.M.; 5 animals per group) | |
|---|---|---|
| | From control animals | From DMV-treated animals |
| 30 minutes | 572 ± 61 | 1020 ± 131 |
| 60 minutes | 710 ± 115 | 1017 ± 128 |

The ability of DMV to reduce the noxious effects of Cyclophosphamide on the chromosome morphology of bone marrow cells was demonstrated in "Chinese hamsters" (Cricetulus griseus) using the method by C. E. Ford and J. L. Hammerton as described in Stain. Technol. 31, 1956, pp. 247–261. The experimental animals were given physiological saline or 50 mg/kg or 100 mg/kg DMV s.c., and 90 minutes later Cyclophosphamide 30 mg/kg i.p. The animals were killed 24 hours after the Cyclophosphamide administration, and the karyotypes of their bone marrow cells were investigated.

As Table VIII shows, DMV decreased the number of cells with chromosomal failures produced by Cyclophosphamide.

TABLE VIII

| | Control | Cyclophosphamide alone | Cyclophosphamide with DMV 50 mg/kg; with DMV 100 mg/kg | |
|---|---|---|---|---|
| Percentage of aberrant mitoses | 0.8% | 62.0% | 43.6% | 35.6% |

(5 animals per group, 100 mitoses per animal analyzed).

What is claimed is:
1. 2-Imino-5-(4-carboxybutyl)barbituric acid.
2. The sodium salt of the acid of claim 1.
3. The potassium salt of the acid of claim 1.
4. The disodium salt of the acid of claim 1.
5. The addition salt of the acid of claim 1 with diethanolamine.
6. The addition salt of the acid of claim 1 with N-methylglucosamine.

* * * * *